United States Patent [19]

Firestone

[11] 4,388,326
[45] Jun. 14, 1983

[54] PHENYL HYDROXYPROPYL SULFOXIDE ENZYME INHIBITORS

[75] Inventor: Raymond A. Firestone, Fanwood, N.J.

[73] Assignee: Merck & Co., Inc., Rahway, N.J.

[21] Appl. No.: 147,657

[22] Filed: May 7, 1980

Related U.S. Application Data

[63] Continuation-in-part of Ser. No. 66,603, Aug. 15, 1979, abandoned.

[51] Int. Cl.$^3$ .................. A61K 31/095; C07C 147/14
[52] U.S. Cl. ..................................... 424/335; 424/94; 424/304; 424/308; 424/250; 424/251; 424/263; 424/270; 424/272; 424/273 R; 424/275; 544/228; 544/318; 546/294; 548/186; 548/228; 548/229; 548/337; 549/66; 260/465 R; 568/32; 568/36; 568/37
[58] Field of Search ...................... 560/17; 568/32, 36, 568/37; 260/465 R; 424/304, 308, 335

[56] References Cited

U.S. PATENT DOCUMENTS

| | | | |
|---|---|---|---|
| 2,812,267 | 11/1957 | Garner et al. | 568/32 |
| 2,864,866 | 12/1958 | Louthan | 568/32 |
| 3,069,471 | 12/1962 | Tashlick | 568/32 |
| 3,369,025 | 2/1968 | Bolhofer | 546/342 |
| 3,652,646 | 3/1972 | Leigh et al. | 424/308 |
| 3,804,904 | 4/1974 | Bentley et al. | 568/37 |
| 3,950,542 | 4/1976 | Kalopissis et al. | 424/316 |

FOREIGN PATENT DOCUMENTS 496639 11/1970 Switzerland .

OTHER PUBLICATIONS

Durst et al., *Can. J. Chem.*, 51(11), 1704–1712 (1973).
Nambara et al., Chem. Abstr., 59, 7411f (1963).
Walsh, "Horizons Biochem. Biophys.", vol. 3, 1977, pp. 36–81.
Mislow et al., "J. Amer. Chem. Soc.", vol. 90, 1968, p. 4869.
Mislow et al., "J. American Chem. Soc.", vol. 92, 1970, p. 2100.
Evans et al., "J. Amer. Chem. Soc.", vol. 94, 1972, p. 3672.

*Primary Examiner*—Donald G. Daus
*Assistant Examiner*—James H. Turnipseed
*Attorney, Agent, or Firm*—William H. Nicholson; Mario A. Monaco

[57] ABSTRACT

Organic sulfoxides having a latent allyl group bound to the sulfur are enzyme inhibitors of the suicide or $K_{cat}$ type.

4 Claims, No Drawings

PHENYL HYDROXYPROPYL SULFOXIDE ENZYME INHIBITORS

BACKGROUND OF THE INVENTION

This is a continuation-in-part of copending application Ser. No. 066,603, filed Aug. 15, 1979 now abandoned.

This invention is concerned with a novel enzyme inhibitor of the suicide or $K_{cat}$ type in which the latent reactive group is an alkylsulfoxide which is in reversible equilibrium with an allyl sulfenate:

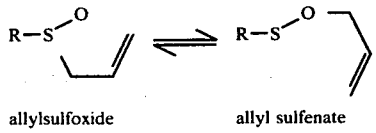

allylsulfoxide      allyl sulfenate (A)

The particular enzyme inhibitor of this invention has structural formula:

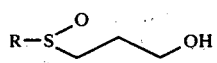

and is an inhibitor of alcohol dehydrogenase and hence useful in the treatment of the symptoms of alcoholism.

Suicide enzyme inhibitors are substances bearing a latent reactive group that is unmasked by the target enzyme itself, and which after being unmasked, immediately reacts with the enzyme in an irreversible manner, inactivating it. Enzyme inhibitors of the suicide type are known in the art but until now almost invariably have employed a Michael acceptor as the reactive species and these are described by Walsh in *Horizons Biochem. Biophys.*, 3, 36-81 (1977).

The allylsulfoxide-allyl sulfenate equilibrium of reaction scheme (A) is also known in the art and has been studied as an interesting chemical reaction by Mislow et al., *J. Amer. Chem. Soc.*, 90, 4869 (1968); 92, 2100 (1970) and Evans et al., *J. Amer. Chem. Soc.*, 94, 3672 (1972). Generally, allylsulfoxides are unreactive, but allyl sulfenates are highly reactive electrophiles, and would be expected to capture almost any nucleophile (Nu) in an enzyme that happens to be near it at the moment it is formed:

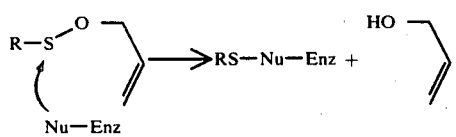

(B)

Usually the nucleophile is one from the protein portion (prosthetic group) of the enzyme, such as a sulfhydryl, amino, hydroxy, imidazolyl or the like. Once the nucleophile is sulfenylated, the enzyme is altered from its native, active form and can no longer function in its intended role as a biochemical catalyst.

In the present invention, the latency of the allylsulfoxide group is secured as a propanol which is not especially reactive. However, in the properly designed inhibitor, the target enzyme recognizes it as a potential substrate, and removes the α- and β- protons creating the enol, which in this case is also an allyl sulfoxide:

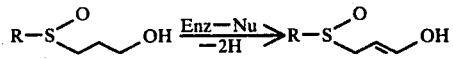

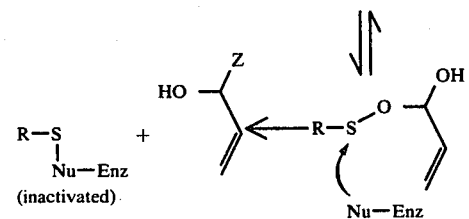

In either case, the allylsulfoxide can now rearrange to the allyl sulfenate which captures the enzyme's nucleophile, inactivating it.

It is, therefore, an object of this invention to provide a novel organic sulfoxide wherein one of the substituents on the sulfur is a latent allyl group which becomes unmasked upon reaction with the target enzyme and which functions as an enzyme inhibitor of the suicide type.

It is another object of this invention to provide a useful tool of biochemical research in the form of a selective, very active enzyme inhibitor.

It is a further object of this invention to provide a means for inhibiting the enzyme alcohol dehydrogenase, both in vitro and in vivo with the novel organic sulfoxide of this invention.

It is a still further object to provide a method of treating the symptoms of alcoholism, the progress of which is partly dependent on the activity of the enzyme alcohol dehydrogenase, which comprises the administration of an effective amount of the enzyme inhibitor of this invention.

It is also an object of this invention to provide pharmaceutical formulations comprising the novel enzyme inhibitor of this invention.

DETAILED DESCRIPTION OF THE INVENTION

This invention comprises, as one embodiment, the novel compound of formula:

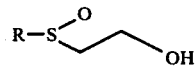

wherein
R is
(a) phenyl, either unsubstituted or substituted with such as
  (1) nitro,
  (2) cyano,
  (3) $C_{1-3}$ alkylsulfonyl,
  (4) $C_{1-3}$ alkoxycarbonyl,
  (5) o-$C_{1-3}$ alkyl,
  (6) o,o-di($C_{1-3}$ alkyl), or
  (7) di(trifluoromethyl);
(b) trihalomethyl, such as trifluoromethyl or trichloromethyl;
(c) heteroaryl such as
  (1) thiazolyl,
  (2) imidazolyl,
  (3) pyridinyl,
  (4) pyrazinyl,
  (5) oxazolyl, (6) pyrimidinyl, or
(7) thienyl.

The novel enzyme inhibitor of this invention has a high, specific activity and thus is a useful tool for the research biochemist and pharmacologist in studies of biochemical changes involving alcohol dehydrogenase in vitro, and in vivo, and in biochemical assays for natural enzyme substrates and the like. The enzyme inhibitor is active, in vitro, at concentrations as low as about 0.1 mM but are generally employed at concentrations of 1 to about 2 mM.

For in vivo studies, the novel enzyme inhibitor of this invention is administered orally or parenterally, preferably the latter and preferably intravenously. Dosages of about 0.1 mg/kg to about 50 mg/kg are used depending on the purpose of the experiment, which may require the use of the threshold dose or the dose to produce total inhibition of the particular enzyme.

The novel enzyme inhibitor of this invention is useful in the treatment of the symptoms of alcoholism when administered at from 0.1 to about 500 mg/kg body weight, preferably at from 1 to about 50 mg/kg of body weight. Any of the usual pharmaceutical oral forms may be employed such as tablets elixirs, aqueous suspensions or the like comprising from about 0.1 to about 500 mg of the compounds of this invention. Sterile solutions for injection comprising from about 0.1 to about 500 mg of the compounds of this invention given two to four times daily are also suitable means of delivery.

The novel process for preparing the novel compounds of this invention comprises oxidation of an aromatic thio compound of structure:

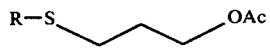

wherein R is as previously defined and Ac is $C_{1-4}$ alkanoyl.

The oxidizing agent is such as 1-chlorobenzotriazole, $H_2O_2/V_2O_5$, $SO_2Cl_2/H_2O$/silica gel, $Cl_2$, $Br_2$, $NaIO_4$, acetyl nitrate, $Tl(NO_3)_3$, or a peracid such as m-chloroperbenzoic acid, preferably the latter. The oxidation with a peracid is conducted at temperatures from $-70°$ C. to about $30°$ C., preferably at about $0°-25°$ C., in an organic solvent such as an aromatic solvent, for example benzene, toluene or the like; or a chlorinated hydrocarbon such as tetrachloroethylene, chloroform, methylene chloride or the like, for times of a few minutes to about 4 hours.

After the oxidation is substantially complete, the protective group, Ac, is removed by a standard procedure such as treatment with a strong organic acid such as trifluoroacetic acid, a strong mineral acid such as hydrochloric acid or a strong base such as sodium hydroxide or potassium hydroxide. It is preferred to use an alkali metal hydroxide in a lower alkanol such as methanol or ethanol at about 15° to about 50° C., conveniently at room temperature for about 1 to about 6 hours.

EXAMPLE 1

3-p-Nitrophenylsulfinyl-1-propanol

Step A: Preparation of 3-p-nitrophenylthio-1-propyl acetate (I)

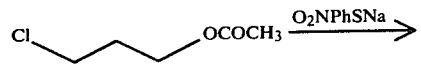

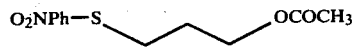

3-Chloro-1-propyl acetate, 137 mg (1 mmole), is stirred with 177 mg of sodium p-nitrophenylthiolate (1 mmole) in 10 ml of acetonitrile at room temperature for 6 hours. The solvent is evaporated and replaced by ethanol. The ethanol solution is filtered and evaporated to afford compound I.

Step B: Preparation of 3-p-nitrophenylsulfinyl-1-propyl acetate (II)

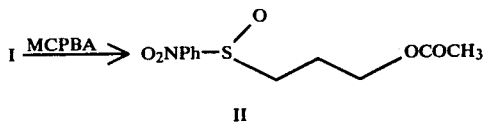

Compound I, 255 mg (1 mmole), in 20 ml of $CH_2Cl_2$ is treated at $0°$ C. over 1 hour with a solution of 203 mg of MCPBA (85%; 1 mmole) in 20 ml of $CH_2Cl_2$. The reaction is aged 30 minutes at $25°$ C., washed with aqueous $NaHCO_3$ and evaporated to afford compound II.

Step C: Preparation of 3-p-nitrophenylsulfinyl-1-propanol (III)

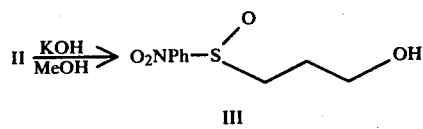

Compound II, 271 mg, is stirred at $25°$ C. for 3 hours with a solution of 57 mg of KOH (1 mmole) in 20 ml of MeOH. The solvent is evaporated and the residue is partitioned between water and ethyl acetate. Evaporation of the ethyl acetate yields compound III.

Employing the procedures substantially as described in Example 1, Steps A through C, but substituting for the sodium p-nitrophenylthiolate used in Step A, an equimolar amount of the compound R-SH, wherein R is
(a) phenyl, either unsubstituted or substituted with such as
 (1) nitro,
 (2) cyano,
 (3) $C_{1-3}$ alkylsulfonyl,
 (4) $C_{1-3}$ alkoxycarbonyl,
 (5) o-$C_{1-3}$ alkyl,
 (6) o,o-di($C_{1-3}$ alkyl), or
 (7) di(trifluoromethyl);
(b) trihalomethyl, such as trifluoromethyl or trichloromethyl;
(c) heteroaryl such as
 (1) thiazolyl,
 (2) imidazolyl,
 (3) pyridinyl,
 (4) pyrazinyl,
 (5) oxazolyl,
 (6) pyrimidinyl, or
 (7) thienyl;
there is produced the corresponding compounds of structure

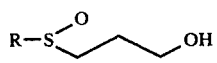

EXAMPLE 2

Tablets containing 1.0, 2.0, 25.0, 50.0 and 100.0 mg, respectively of 3-p-nitrophenylsulfinyl-1-propanol (active compound) are prepared as illustrated below:

|  | Amount - mg/tablet | | | | |
| --- | --- | --- | --- | --- | --- |
| Active Compound | 1.0 | 2.0 | 25.0 | 50.0 | 100.0 |
| Microcrystalline cellulose | 49.25 | 48.75 | 37.25 | 100.0 | 200.0 |
| Modified food corn starch | 49.25 | 48.75 | 37.25 | 4.25 | 8.5 |
| Magnesium stearate | 0.50 | 0.50 | 0.50 | 0.75 | 1.5 |

All of the active compound cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 50.0 mg, and 100.0 mg of active compound per tablet.

| Injectable Preparation | |
| --- | --- |
| 3-p-nitrophenylsulfinyl-1- | |
| propanol | 25 mg |
| Pyrogen fee water to | 1 ml |

Sterilize by filtration and seal under nitrogen.

What is claimed is:

1. The compound 3-p-nitrophenylsulfinyl-1-propanol or a pharmaceutically acceptable salt thereof.

2. A pharmaceutical enzyme inhibiting composition comprising a pharmaceutical carrier and an effective enzyme inhibiting amount of the compound 3-p-nitrophenylsulfinyl-1-propanol or a pharmaceutically acceptable salt thereof.

3. A method of inhibiting alcohol dehydrogenase in a patient in need of such treatment which comprises the administration of an enzyme inhibitory amount of a compound of structural formula:

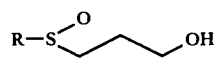

or a pharmaceutically acceptable salt thereof wherein R is
(a) phenyl, either unsubstituted or substituted with
  (1) nitro,
  (2) cyano,
  (3) $C_{1-3}$ alkylsulfonyl,
  (4) $C_{1-3}$ alkoxycarbonyl,
  (5) o-$C_{1-3}$ alkyl,
  (6) o,o-di($C_{1-3}$ alkyl), or
  (7) di(trifluoromethyl).

4. The method of claim 3 wherein the compound is 3-p-nitrophenylsulfinyl-1-propanol.